United States Patent [19]
Elledge

[11] Patent Number: 4,793,806
[45] Date of Patent: Dec. 27, 1988

[54] DENTAL DOWEL PIN

[76] Inventor: Paul Elledge, 1718 Salem, Deer Park, Tex. 77536

[21] Appl. No.: 43,744

[22] Filed: Apr. 29, 1987

[51] Int. Cl.⁴ .............................................. A61C 19/00
[52] U.S. Cl. ..................................................... 433/74
[58] Field of Search ....................... 433/74, 34; 264/16

[56] References Cited

U.S. PATENT DOCUMENTS

| 4,056,585 | 11/1977 | Waltke | 433/74 |
| 4,238,189 | 12/1980 | Tirino | 264/16 |
| 4,449,931 | 5/1984 | Saito | 433/34 |

FOREIGN PATENT DOCUMENTS 866118  4/1961  United Kingdom .................. 433/74

Primary Examiner—John J. Wilson
Attorney, Agent, or Firm—Richard C. Litman

[57] ABSTRACT

A dental dowel pin includes an improved geometry for increasing the accuracy of placement of a tooth die in a base support in the dental laboratory, and for maintaining this accuracy despite dust or wear of the dowel or its retaining slot in said base support. The body is of generally oval cross section with side and end walls normally to a horizontal plane and a plurality of inverse angle indentations and fits accurately into a slot of negative impression in the base during utilization of the invention. The dental dowel pin of the invention has a knurled cylindrical head on an end that is insertable into a cast model die.

10 Claims, 1 Drawing Sheet

DENTAL DOWEL PIN

BACKGROUND OF INVENTION

1. Field of Invention

Fixed prosthetics (crown and bridge) modeling requires the molding of cast tooth die sections, typically each with 1-3 teeth on a cast model with a base support. The body of the dental dowel pin fits into a slot in the base formed by insertion of the dowel pin into the base while the mix is in liquid form. Thus the base forms the negative impression of the pin. The head part of the dental dowel pin, which is typically a small cylindrical knurled or grooved rod, is held fast in the die section itself.

A typical ordinary dowel pin is made of tapered brass, the smaller end of which fits into a retaining slot. It may have one or two flat sides to prevent rotation when fully engaged in the base, but as a result of its taper, such a dowel pin sacrifices retention ability at the base of the pin and furthermore dust or wear will soon limit the accuracy of alignment possible with the model with which the pin is used.

In the case of the present invention, the geometry of the dowel pin is specially shaped to eliminate the taper, and the sides of the dowel pin all meet the endplane of the pin at 90° degrees. The centerlines of two inverse angle indentations on opposite sides of the pin also meet the end plane at 90 degrees. The walls of each of these indentations, also at 90 degrees to the end plane, further increase the amount of conjoined walls to assure accurate replacement of the pin no matter how often it is removed and replaced in the course of the dental modeling for which the aforesaid cast are designed to be utilized.

2. Description of the Prior Art

Many existing dowel pin systems utilize a plurality of pins to achieve the desired placement and alignment functions, and otherwise make the processing inconvenient and time consuming. Alternatively, many other dowel pin systems have used sleeves embedded in the base cast that are normally formed by inverting the projecting ends of the dowel pin into the sleeves prior to pouring the base cast material and then letting the material harden around the sleeves. Such sleeves are found to rotate or otherwise lose their alignment upon use. The greater simplicity, stability, accuracy, and ease of utilization of the dental dowel pin of the present invention are advantageous for its utilization in the dental laboratory.

Prior art generally illustrating the field of the invention includes the following U.S. patents:

| Inventor | U.S. Pat. No. |
| --- | --- |
| H. Blitz | 4,443,192 |
| H. Imaizumi | 4,371,340 |
| M. der Avanessian | 4,363,625 |
| W. B. Dragan | 4,139,943 |
| F. M. Kulig, et al. | 3,969,820 |
| R. E. Huffman | 3,937,773 |
| B. Weissman | 3,875,665 |
| P. Eberhard | 3,798,772 |

The Blitz patent (U.S. Pat. No. 4,443,192) discloses a tapered dowel pin with a head portion characterized by a plurality of tooth-engaging barbs. Imaizumi (U.S. Pat. No. 4,371,340) discloses a hard plastic denture model pin of frustoconical geometry with one or two flat sides. Der Avanessian (U.S. Pat. No. 4,363,625) discloses a tapered tool retainer pin of cusped transverse cross section fitting into a cooperative seat mounted in the model base support. Dragan (U.S. Pat. No. 4,139,943) discloses a double pronged pin interconnected by a bridge and a method for making a dental die using the pronged pin. Kulip, et al., (U.S. Pat. No. 3,969,820) discloses a tapered composite dowel pin made of synthetic resin with a planar surface and diametrically opposed rib.

Huffman (U.S. Pat. No. 3,937,773) discloses a dental model with a plurality of parallel nontapered guide pins slidably seated within cylindrical cavities in an apertured retainer. Weissman (U.S. Pat. No. 3,875,665) discloses a tapered pin of elliptical transverse cross section, a mounting post extended in the opposite parallel direction, and a short key structure projected radially from the region of the mounting post. Eberhard (U.S. Pat. No. 3,798,772) discloses a tapered dowel pin that passes through a central plate with an orienting noncircular pedestal forming a socket for the pin. The above prior art examples lack the vertically sided and indented geometry of the present dental dowel pin which offers an increased amount of conjoined area between the pin and its retaining slot.

SUMMARY OF THE INVENTION

The dental dowel pin of the present invention consists of a structural member having a shank shaped as a generally elongated rectangular solid with ends rounded to provide an oval cross section, and wherein a plurality of longitudinal indentations are made to increase the contact area, and thus the retentional accuracy, between the dental dowel pin and the walls of the cavity or slot in the base support into which it is inserted during application. A knurled rod head fastened on the opposite end of the dental dowel pin shank anchors the pin in the cast tooth die. Practical materials of which to construct the dental dowel pin include brass, plastic, and epoxy, but any similarly hard material may be equally satisfactory.

DESCRIPTION OF THE PREFERRED EMBODIMENT

Figure 1:
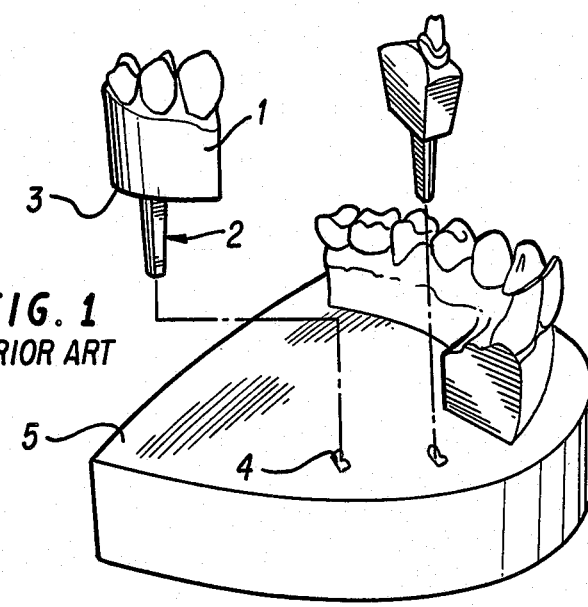
FIG. 1 is a top perspective view of a stone cast and dies with a typical dowel pin.
Figure 2:
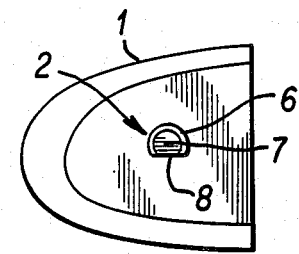
FIG. 2 is a bottom plan view of one of the dies and dowel pin of FIG. 1.
Figure 3:
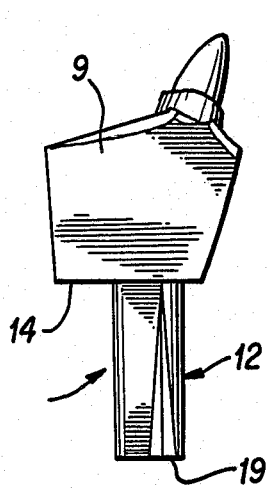
FIG. 3 is a side elevation of the dental dowel pin of the present invention as solidly implanted by means of a knurled head within a cast model tooth die.

FIGS. 1 and 2 depict an example of a prior art dental model wherein each die 1 includes a dowel pin having a shank portion 2 depending from the die bottom wall 3 and adapted to closely fit within a mating cavity 4 as formed within the cooperating stone cast 5. In this example, the dowel pin shank 2 will be seen to be provided with a taper or bevel 6 inclined inwardly from the die bottom wall 3 to the dowel pin bottom wall 7. To provide an asymetrical configuration, a flat 8 is formed along one side of the dowel pin shank 2.

Figure 4:
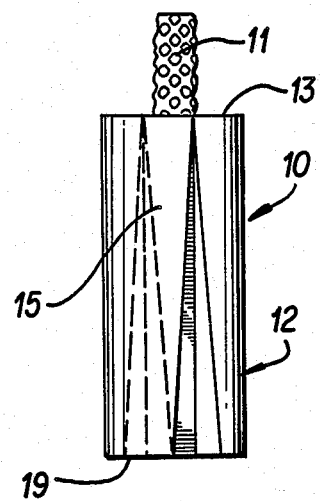
FIG. 4 is a side elevation of the dental dowel pin and head.
Figure 5:
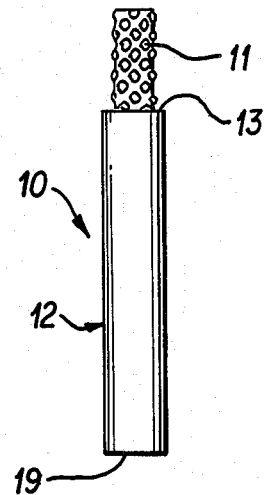
FIG. 5 is an end elevation of the dowel pin of FIG. 4.

The dowel pin of the present invention is illustrated in FIGS. 3-7 wherein it will be seen that the improved dowel pin, generally designated 10, includes a head 11 at its upper end which is knurled or otherwise roughened as shown in FIGS. 4-5 to ensure fixed retention within the produced die 9. This head 11 is joined to a dowel pin shank 12 which having a horizontally disposed top shoulder 13 adapted to about the bottom 14 of the die 9.

Figure 6:
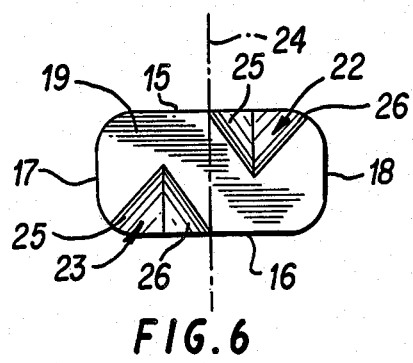
FIG. 6 is a bottom plan view of the dental dowel pin showing the cross-sectional appearance of two inverse angle indentations.
Figure 7:
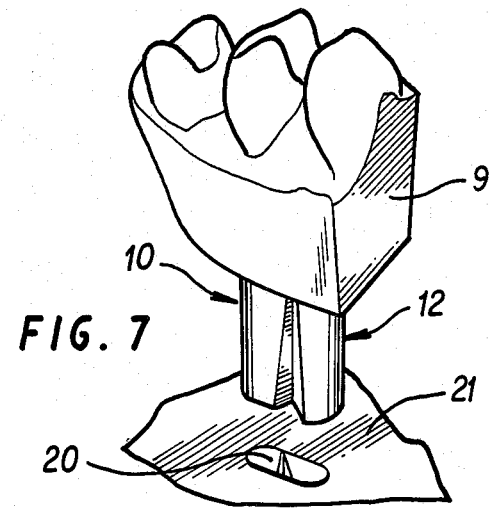
FIG. 7 is a perspective view of the dental dowel pin attached to a cast die and showing the slot in the base support into which the dental dowel pin accurately fits.

The unique construction of the present dowel pin 10 includes the enlarged, oval configuration of the shank 12 as shown most clearly in the bottom view of FIG. 6 of the drawings. This generally rectangular solid body is formed by two substantially parallel side walls 15, 16 joined to two shorter end walls 17, 18 the latter of which may be curved. An important feature is that these side and end walls are disposed substantially normal to both the horizontal top shoulder 13 as well as the shank bottom wall 19. This enlarged oval configuration of the dowel pin shank 12 together with the normal disposition of the side and end walls thereof has been found to greatly enhance the retention of the dowel pin in its mating cavity 20 as formed in the cooperating stone cast 21. This construction is contrary to the majority of prior art devices wherein a tapered dowel pin shank is most commonly employed. It will be appreciated that the very nature of a tapered pin encourages unwanted falling out of a die from its cooperating stone cast.

With the present construction, the enlarged oval configuration of the dowel pin shank periphery will be understood to angularly or arccuately affix the placement of the die in a stone cast with respect to a horizontal plane. Additional orientation or fixation is achieved against unwanted rocking or angular displacement about a vertical axis by means of a pair of inverted V-beveled female channels 22, 23 formed in opposite side walls 15, 16 of the dowel pin shank. As shown most clearly in FIG. 6 of the drawings, one of these channels 22 is disposed on one side of the shank center line 24, adjacent one end wall 18 while the other channel 23 is formed in the other shank side wall 16 on the opposite side of the center line 24, adjacent the other shank end wall 17. Each channel 22, 23 comprises a pair of inclined walls 25-26 which are inclined upwardly and inwardly toward one another and converge at a point immediately beneath the dowel pin shoulder 13. The resultant juncture line 7 between channel walls 25 and 26 thus will be seen to be inclined upwardly and outwardly from the bottom wall 19 of the dowel pin shank toward the shank shoulder 13.

The foregoing described arrangement provides a dowel pin construction which ensures a more secure and accurate positioning and retention of a tooth die with respect to its associated cast.

What is claimed is:

1. A dental dowel pin comprising:
    a shank defining a generally rectangular solid member having substantially parallel side walls joined to shorter end walls to form a shank periphery of substantially oval cross-section;
    a plurality of inverse angular channels in said shank periphery;
    one said channel in each said side wall adjacent respective opposite ones of said end walls; and,
    said channels being on opposite sides of a transverse center line bisecting said side walls.

2. The dental dowel pin of claim 1 including, a knurled head on one end of said shank for anchoring said dowel pin within a cast tooth die model.

3. The dental dowel pin of claim 1 wherein, each said channel includes a pair of intersecting upwardly and outwardly directed walls.

4. The dental dowel pin of claim 1 wherein, said shank includes a substantially horizontal top shoulder and bottom wall, and said side and end walls are substantially normal to said top shoulder and bottom wall.

5. A dental dowel pin comprising:
    a shank defining a generally rectangular solid member having a pair of longer sides, said longer sides parallel to each other, and having a pair of shorter sides, said shorter sides parallel to each other, whereby said longer and said shorter sides of said shank do not taper and the cross-section of said shank is substantially rectangular throughout the entire length of said shank; and
    a plurality of longitudinally extending, inverse angular channels disposed in said shank.

6. The dental dowel pin of claim 5 including a knurled head on one end of said shank for anchoring said dowel pin within a cast tooth die model.

7. The dental dowel pin of claim 5 including, one said channel incised in each said longer side adjacent to respective opposite ones of said shorter sides.

8. The dental dowel pin of claim 5 wherein, each said channel includes a pair of intersecting upwardly and outwardly directed walls.

9. The dental dowel pin of claim 5 wherein, said shank includes a substantially horizontal top shoulder and bottom wall, and said longer and shorter sides are substantially normal to said top shoulder and said bottom wall.

10. The dental dowel pin of claim 5 wherein, said channels are on opposite sides of a transverse center line bisecting said shorter sides.

* * * * *